United States Patent
Rusch et al.

(10) Patent No.: US 7,232,547 B2
(45) Date of Patent: Jun. 19, 2007

(54) APPARATUS AND METHOD FOR TESTING AND CONTINUOUSLY READING LOW-VOLUME SAMPLES

(75) Inventors: Terry L. Rusch, Marshfield, WI (US); James L. Weber, Marshfield, WI (US); Mitchel J. Doktycz, Knoxville, TN (US); Kim M. Fieweger, Marshfield, WI (US); Jon P. Chudyk, Marshfield, WI (US); J. Steven Hicks, Knoxville, TN (US); Jianhong Che, Marshfield, WI (US)

(73) Assignee: Marshfield Clinic, Marshfield, WI (US)

( * ) Notice: Subject to any disclaimer, the term of this patent is extended or adjusted under 35 U.S.C. 154(b) by 608 days.

(21) Appl. No.: 10/394,811

(22) Filed: Mar. 21, 2003

(65) Prior Publication Data

US 2004/0071599 A1 Apr. 15, 2004

Related U.S. Application Data

(60) Provisional application No. 60/366,885, filed on Mar. 22, 2002.

(51) Int. Cl.
*B32B 5/02* (2006.01)
(52) U.S. Cl. .................. 422/66; 422/82.05; 422/99; 422/100; 422/101; 436/94; 436/172; 436/180; 435/287.2
(58) Field of Classification Search ............ 436/172, 436/180, 94; 422/68.1, 99–101, 66, 82.05; 435/287.2
See application file for complete search history.

(56) References Cited

U.S. PATENT DOCUMENTS

| | | | |
|---|---|---|---|
| 3,620,678 A | | 11/1971 | Guigan et al. |
| RE28,339 E | | 2/1975 | Maxon |
| 3,923,463 A | | 12/1975 | Bagshawe et al. |
| 3,979,264 A | | 9/1976 | Buerger |
| 4,094,127 A | | 6/1978 | Romagnoli |
| 4,130,230 A | | 12/1978 | Seitz |
| 4,264,560 A | * | 4/1981 | Natelson ............... 422/58 |
| RE30,627 E | | 5/1981 | Bagshawe et al. |
| 4,327,073 A | | 4/1982 | Huang |
| 4,341,735 A | | 7/1982 | Seifried |
| 4,506,495 A | | 3/1985 | Romagnoli |
| 4,826,337 A | | 5/1989 | Unuma |
| 4,836,431 A | | 6/1989 | Hirth et al. |
| 4,853,059 A | * | 8/1989 | Meguro et al. ............ 156/157 |
| 4,878,971 A | | 11/1989 | Tsunekawa et al. |

(Continued)

OTHER PUBLICATIONS

"Automated Systems Move to a Smaller Scale", R&D Magazine, Jan. 2002, pp. A3-A5.*

(Continued)

*Primary Examiner*—Jill Warden
*Assistant Examiner*—Jyoti Nagpaul
(74) *Attorney, Agent, or Firm*—Hamilton, DeSanctis & Cha, LLP.

(57) ABSTRACT

The present invention is directed to a well sampling tape (otherwise known as "microwell tape" or simply "tape"), a dispenser for dispensing small volumes of liquid into the wells formed in the tape and a detector for high-throughput sample reading of the liquid dispensed in the individual wells. The present invention is more specifically directed to a bioassay system incorporating the materials listed above.

28 Claims, 11 Drawing Sheets

U.S. PATENT DOCUMENTS

| | | | |
|---|---|---|---|
| 4,952,266 A | 8/1990 | Tsuruta et al. | |
| 4,978,505 A | 12/1990 | Kertz | |
| 5,092,466 A | 3/1992 | Anderson | |
| 5,200,148 A | 4/1993 | Saito | |
| 5,207,986 A | 5/1993 | Kadota et al. | |
| 5,213,766 A | 5/1993 | Flesher et al. | |
| 5,525,302 A | 6/1996 | Astle | |
| 5,648,266 A | 7/1997 | Astle | |
| 5,736,105 A | 4/1998 | Astle | |
| 5,789,251 A | 8/1998 | Astle | |
| 5,810,170 A | 9/1998 | Alvite | |
| 5,827,745 A | 10/1998 | Astle | |
| 5,882,597 A | 3/1999 | Astle | |
| 5,958,343 A | 9/1999 | Astle | |
| 6,245,297 B1 | 6/2001 | Kowallis | |
| 6,274,374 B1 | 8/2001 | Astle | |
| 6,284,546 B1 | 9/2001 | Bryning et al. | |
| 6,355,487 B2 | 3/2002 | Kowallis | |
| 6,537,752 B1 | 3/2003 | Astle | |
| 6,610,470 B2 | 8/2003 | Blumenfeld et al. | |
| 6,632,653 B1 | 10/2003 | Astle | |
| 6,733,729 B2 | 5/2004 | Blumenfeld et al. | |
| 6,784,982 B1 | 8/2004 | Blumenfeld et al. | |
| 6,867,851 B2 | 3/2005 | Blumenfeld et al. | |
| 6,878,345 B1 * | 4/2005 | Astle | 422/102 |
| 2001/0051714 A1 | 12/2001 | Chen et al. | |
| 2002/0001546 A1 | 1/2002 | Hunter et al. | |
| 2002/0013958 A1 | 1/2002 | Lalgudi et al. | |
| 2002/0025575 A1 | 2/2002 | Malin et al. | |
| 2002/0041829 A1 | 4/2002 | Kowallis | |
| 2002/0055179 A1 | 5/2002 | Busey et al. | |
| 2002/0084214 A1 | 7/2002 | Astle | |
| 2002/0098121 A1 | 7/2002 | Astle | |
| 2002/0136666 A1 | 9/2002 | Astle | |
| 2004/0071599 A1 | 4/2004 | Rusch et al. | |

OTHER PUBLICATIONS

"*Microtape*™ System", Tomtec Brochure, Jan. 21, 2002 (8 pages)*.
"Small Volume Assay System", Tomtec Brochure, Dec. 13, 1999 (7 pages).
"Microplate Sealing", Tomtec Website http://www.tomtec.com/Pages/microplate_sealing.html, Apr. 3, 2002 (2 pages).
"Auto Seal", Tomtec Website http://www.tomtec.com/Pages/AutoSeal.html (2 pages).
"Quadra-Wash 2", Tomtec Website http://www.tomtec.com/Pages/Qwash2.html (2 pages).
"Quadra 3 Nanoliter Transfers", Tomtec Website http://www.tomtec.com/Pages/Q3nanoliter.html (2 pages).
"New Dispensing Options", Tomtec Website http://www.tomtec.com/Pages/Newdispensing.html (1 page).
"SynQUAD Technology", Cartesian Technologies, Inc. Website http://www.cartesiantech.com/sq_tech.html (3 pages).
"NanoFill™ 8—Optimized for Bulk Dispense", Innovadyne Technologies, Inc. Brochure (1 page).

* cited by examiner

APPARATUS AND METHOD FOR TESTING AND CONTINUOUSLY READING LOW-VOLUME SAMPLES

REFERENCE TO RELATED APPLICATION

The application claims priority to U.S. Provisional Application entitled "Apparatus and Method for Testing and Continuously Reading Low-volume Samples," Ser. No. 60/366,885 filed Mar. 22, 2002, which is incorporated herein by reference in its entirety.

STATEMENT REGARDING FEDERALLY SPONSORED RESEARCH

This invention was made, in part, with United States government support awarded by National Institutes of Health Grant Nos. N01-HV48141 and R01HL62681-01. The United States may have certain rights in the invention.

FIELD OF THE INVENTION

The present invention is directed to a well sampling tape (otherwise known as "microwell tape" or simply "tape"), a dispenser for dispensing small volumes of liquid into the wells formed in the tape, a sealer for sealing the contents of the wells in the tape, a water bath thermocycler for inducing the reactions and a detector for high-throughput sample reading of the reaction products contained in the individual wells. The present invention is more specifically directed to a bioassay system incorporating the materials listed above.

BACKGROUND OF THE INVENTION

In the biotechnology industry, there is an ongoing need to develop faster and more economical bioassay systems to test and screen compounds. The current standard format is a microwell or microtiter plate having a dimension approximately 3×5 inches and including 96 wells. Higher density systems using 384-wells are now being incorporated into the research industry. However while the plates comprise more wells, they still have the drawbacks associated with individual plates: the need for storing plates, labeling them and analyzing each plate individually. Often, the tasks associated with such plates are accomplished by hand, including pipetting and syringe dispensing. While this work is tedious and time consuming, when magnified by 384 for each well of the plate, it is even more so. In addition, hand pipetting and syringe dispensing are generally only accurate to 1 microliter (ul) and above.

One problem encountered with sample handling of the prior art is demonstrated by small-volume polymerase chain reaction (PCR) assays. Single nucleotide polymorphisms (SNPs) represent the most abundant type of sequence variation in the human genome and can and should be useful tools for many diverse applications, including delineating the genetic architecture of complex traits and diseases, pharmacogenetics, forensics and evolutionary studies.

Historically, genetic studies have been predicated on identifying and employing genetic variation to address problems of biological significance. An impressive SNP resource already exists as several hundreds of thousands have been deposited into publicly accessible databases, such as the National Center for Biotechnology Information's dbSNP and others. However, without parallel progress in SNP genotyping technology, the use of any database is seriously circumscribed. In addition to SNPs, other allelic variations provide abundant information on genetic variation, population dynamics, genetic mutations and disease diagnostics. Insertion/Deletion (indel) Polymorphisms are a class of polymorphisms based on length differences among nucleotide alleles. The best current estimate is that 20% of all human polymorphisms are of the insertion/deletion (indel) type. Indels can be broken down into a roughly 50:50 mix of multiallelic and diallelic polymorphisms. Multiallelic indels include the minisatellites (also called VNTRs) and the short tandem repeat polymorphisms (STRPs) (also called microsatellites or simple sequence length polymorphisms (SSLPs)). Minisatellites are relatively rare and typically have repeat lengths of a few tens of nucleotides with tandem repeat copy numbers in the hundreds to thousands. STRPs are abundant and have repeat lengths of 1-6 nucleotides with tandem repeat copy numbers, mostly <30. Diallelic indels are also common, but are only just now beginning to be studied in detail (see below). All of the diallelic indels and most of the STRPs have the desirable feature of being able to be analyzed simply by PCR followed by gel electrophoresis. Indels are believed to be an attractive alternative to SNPs.

Novel genotyping methods amenable to high-throughput analysis should ideally be gel-free, robust, inexpensive and simple to perform. To this end, these requirements have inspired the development of a variety of genotyping assays, including the oligonucleotide ligation assay "OLA" (Landegren, U., et al. (1988) *Science* 241: 1077-80); genetic bit analysis "GBA" (Nikiforov T. T., et al. (1994) *Nucleic Acids Res.* 11:4167-75); mass spectroscopy (Griffin, T. J., et al. (1999) *Proc. Natl. Acad. Sci.* 25: 6301-6306), "chip" technology (Wang., et al, supra), TaqMan (Livak, K. J., et al. (1995) *PCR Methods Appl.* 4:357-62) and dynamic allele specific hybridization "DASH" (Howell, W. M., et al. (1999) *Nat. Biotechnology* 17:87-88). Although many SNP genotyping methods have been developed, no single technology has emerged as being clearly superior due to limitations such as cost, complexity and accuracy.

Recently, new methods for SNP genotyping, in which the primers are labeled with a fluorophor, have been reported (Myakishev, M. et al. (2001) *Genome Res.* 11:163-169). This method relies on PCR amplification of genomic DNA with two tailed allele-specific primers that introduce priming sites for universal primers having the fluorescent tag. The fluorophors are selected to emit at different wavelengths and are thus seen as different colors, in this case red and green. The reactions are carried out in a microtiter plate, and following the reaction the plate is read by a fluorescence plate reader. Identification of the emitted color identifies which specific primer annealed to the genomic DNA, and determination of which primer was used indicates which allele is present in the genomic copy. Of note, the authors found that 40 ng of DNA per 20 ul reaction in a 96 well plate was optimal.

Other systems are described in the following patents, published patent applications and references ("references"). While the references attempt to automate or increase the sensitivity of the disclosed inventions, they are limited to specific applications or are limited by large volumes of samples and reactants.

U.S. Pat. No. Re 28,339 to Maxon describes an analysis system for the multiple analysis of a single sample. This system comprises a transfer strip made from an elongated tape having a plurality of liquid samples adsorbed thereto. The tape is used in conjunction with an analyzing apparatus such that each adsorbed aliquot of the sample may be analyzed by a separate system. The disclosure is limited to sample adsorption as a means of retaining the sample on the tape. In addition, since the retention method is adsorption, the detection method is limited to the sample that is adsorbed thereto, not the product of a reaction that occurs within the tape.

U.S. Patent Application 2002/0001546 to Hunter et al. describes methods for screening substances in a microwell array. The method requires loading an array of capillary tubes having dispensing ends, disposing each dispensing end in proximity to a distinct through-hole and transferring the liquids through the through-holes of the platen through the capillary tubes. The method is directed toward a means of filling the wells rather than providing a substitute to the microtiter plates already present in the prior art. In addition, the method described by Hunter et al. is disadvantaged by using relatively large volumes of about 1 ul.

U.S. Pat. No. 3,979,264 to Buerger describes a band for carrying out microbiological examinations. The band resembles a tape or strip having depressions which hold nutrient media or agar. Bacteria are spotted on the media. The tape can be rolled or folded for incubation or storage. The disclosure does not contemplate a means of analysis but, rather, is limited to a means of maintaining organisms in a nutrient media.

U.S. Pat. No. 3,620,678 to Guigan describes a system for multiple automatic analysis. The system includes a tape resembling a roll of film having holes along its side such that the film can be automatically driven by means of a pin or sprocket. The tape is formed from two layers such that there are cells composed within the tape. One facet of the invention includes the automatic filling of the cells with samples to be analyzed. Means of analysis is contemplated to be spectrophotometric, and the detector system is envisioned to be capable of automatically driving the film through the detector for its analysis. However, the samples are only present in a single suspension, not components of a reaction, and the volumes are quite large, about one cubic centimeter.

U.S. Pat. Nos. 6,355,487 and 6,254,297 and U.S. Published Patent Application 2002/0041829 to Kowallis describe a method and apparatus for transferring small volumes of substances. The apparatus comprises a conveyor belt having a plurality of substrates, the substrates being adapted to hold microtubes such that the tubes can be inserted into the substrate and reagents added to the tubes as the conveyor belt moves along. In another embodiment, the conveyor belt itself may be adapted to comprise substrates such that microtubes can be inserted directly into the wells of the conveyor belt. The apparatus does not include a method for analysis, but is envisioned to provide a method for the production of microarrays allowing for the analysis of samples.

U.S. Pat. No. 6,284,546 to Bryning et al. discloses a method and device for photodetection. The device comprises a means of placing a drop of a sample and reagent liquids on a planar support such that the droplets are allowed to mix. The planar support is movable such that the support can be moved through a detector and the emitted light quantified.

U.S. Pat. No. 5,207,986 to Kadota et al. discloses an apparatus for the automatic analysis of biological samples comprising a conveyor belt system for conveying a sample rack, a rack storage unit, an analysis unit and an identification unit such that the analysis unit identifies the samples in the rack.

U.S. Pat. No. 5,092,466 to Anderson describes an apparatus and method for storing samples of protein gene products, cells or DNA. The samples are sealed in packets which are then attached to film. The film can be labeled such that the packets are accurately identified. The invention is to be utilized in the storage and inventory of biological samples, but is not used or contemplated for use as a reservoir for containing a reaction.

U.S. Patent Application 2002/0055179 to Busey et al. describes an apparatus and method for ultra-high-throughput fluorescent screening of samples. The samples are held in a microtiter plate having V-shaped wells. The apparatus comprises at least two light guides such that a light source adjacent to the plate can illuminate an individual well and the emitted light can be guided to an adjacent detector.

U.S. Pat. Nos. 3,923,463 and Re 30,627 to Bagshawe et al. describe an apparatus for performing chemical and biological analysis. The invention describes a method for the handling of large numbers of samples where sample tubes are loaded into racks, the racks loaded into cassettes and the cassettes transferred from station to station for appropriate dilution, reagent addition and analysis.

While these references attempt to provide means to more easily store and analyze samples, they suffer from certain inadequacies: they use relatively large sample volumes; and they represent isolated steps in reacting samples, adding reaction mixtures, analyzing the reaction products and storing those products for further analysis.

There is a need to develop automation on a much smaller scale. As described in *R&D Magazine* (January 2002, pp A3-A5), companies are now moving to "nanotechnology," i.e., working in the nanoscale range. There is a definite trend for an assay system that is precise, accurate, efficient, small and economical, yet has a high-throughput.

Companies, such as TOMTEC (Hamden, Conn.), Cartesian Technologies (Irvine, Calif.), Gilson, Inc. (Middleton, Wis.), Molecular Devices Corporation (Sunnyvale, Calif.) and Zymark Corp. (Hopkinson, Mass.), have all moved toward developing smaller, faster systems.

Current technology uses "microwell" or "microtiter" plates having volumes ranging from 1 to 1000 μl to prepare samples and contain reactions. Plates of this nature are injection molded, and the larger well volumes are not suitable for very small volumes in the nanoliter (nl) range. In addition, nanoliter wells may require a special shape in order to position the contents optimally for mixing in the well. Therefore, a more optimally designed well is needed to position and contain the sample.

For high-throughput screening, a continuous process is needed for optimum performance and reduced cost. As may be appreciated, an ability to run large quantities of reactions in very small volumes is limited by at least four factors. First, very low-volume reactions are much more susceptible to operator error in pipetting and transferring of samples and reagents. Second, if an appropriate detector is not available to analyze the reaction products efficiently within their margin of error, small-volume reactions are not worthwhile. Third, if manual manipulations are required, the time needed to process the sample is not affected regardless of the reaction volume. Fourth, a combination of the first three deficiencies limits the overall reproducibility of the analysis. Some laboratories have started to use rail systems to form an assembly line type operation for sample handling with microtiter plates and to minimize manual handling. However, these systems are limited by the constraints of the microtiter plate itself.

TOMTEC is currently developing a MICROTAPE system, which is an endless track of microwells formed on a plastic tape for conducting assays. However, each well is circular in format and requires a relatively large volume (>1 microliter) of reagent to obtain reproducible results. In addition, TOMTEC has a method for sealing the microwell tape comprising heat sealing with a covering tape. One problem with this method is that it requires perforations in the sealing tape to release trapped air, as well as a vacuum device to assure flat juxtaposition of the sealing tape to the microwell tape. Further, use of a microwell tape device for sample screening is hindered by the lack of a detector capable of analyzing the contents of the wells.

Currently, there is no method or device suitable for the continuous, small-volume, high-throughput analysis of tagged biological samples. Commercial units require manual manipulation and volumes in the microliter range. Therefore, there is a need for a continuous feed-through unit to perform sample analysis of a large number of very low-volume reactions without extra handling of the reaction mixtures.

SUMMARY OF THE INVENTION

The present invention is directed to a well sampling tape having a continuous length and containing a plurality of wells. The tape has at least one edge defined by a continuous row of indexing perforations.

The present invention is also directed to a sample characterization system utilizing a microwell tape for analysis of samples. The microwell tape has a continuous length and contains a plurality of wells. The tape has at least one lateral edge defined by a continuous row of indexing perforations. The system comprises a drive mechanism adapted to automatically advance the microwell tape; at least one dispenser for dispensing reagents into the wells of the microwell tape; and sealing means for sealing the wells of the microwell tape The present invention is further directed to a system for automatically analyzing a large number of small-volume samples. The system includes the following elements:
 a. a microwell tape having a continuous length and containing a plurality of wells, the tape having first and second lateral edges defined by a continuous row of indexing perforations;
 b. a drive mechanism adapted to move the microwell tape through the system;
 c. a pipetter for transferring samples to the wells of the microwell tape.
 d. a dispenser for transferring a reagent to the well of the microwell tape;
 e. sealing means for sealing the wells of the microwell tape;
 f. a thermocycler; and
 g. a detector for analyzing the contents of wells of the microwell tape.

Further, the present invention is directed to a drive mechanism for moving a continuous tape having indexing perforations. The drive mechanism comprises a motor, a forward and rear belt drum, wherein one of the drums is engaged to the motor; and at least one belt movably affixed to the forward and rear belt drum, the belt including a series of pins adapted to engage indexing perforations of the tape.

The present invention is also directed to a system for automatically analyzing a large number of small-volume samples. The system comprises a microwell tape having a continuous length along the Y-axis and containing a plurality of wells. The wells are optimized to hold submicroliter or nano-volumes of samples for analysis, wherein the microwell tape has indexing perforations regularly spaced along the lateral margins of the tape. The system also includes a drive mechanism, comprising a pinned drive belt (similar to a sprocket), the pinned drive belt being driven by a motor such that the belt can be driven in a forward and backward direction, wherein the pinned drive belt has pins regularly spaced along its length and wherein the pins are dimensioned and configured to matingly engage the indexing perforations of the microwell tape, whereby the microwell tape can be advanced or reversed through an instrument. Further, the system includes a pipetter having a pin array comprising a plurality of pins, wherein the pipetter is affixed to a transom such that the pipetter can move in the X and Z axes and wherein the pipetter is indexed to a sample container and the microwell tape such that the pipetter can transfer samples from the sample container to the microwell tape and wherein the drive mechanism advances the tape along the Y-axis after the sample has been transferred to the microwell tape.

The system also includes a dispenser having a solenoid valve adapted to dispense submicroliter volumes of reagents, wherein the dispenser is affixed to a transom such that the dispenser can move in the X and Z axes and wherein the dispenser is indexed to a sample container and the microwell tape such that the dispenser can transfer samples from the sample container to the microwell tape and wherein the drive mechanism advances the tape along the Y-axis after the reagent has been transferred to the microwell tape. The system further includes a sealer comprising an indexing drum, a heat drum and sealer tape, wherein the heat drum is under tension and juxtaposed to the indexing drum and wherein the indexing drum has a plurality of cavities in register and dimensioned and configured to reflect the bottom profiles of the wells of the microwell tape and wherein the microwell tape matingly engages with the cavities in the indexing drum, wherein the sealer tape is juxtaposed to the upper surface of the microwell tape and wherein advancing the indexing drum forces the microwell tape and the sealer tape under the heat drum whereby the sealer tape is sealed to the microwell tape thereby sealing the wells of the microwell tape. The system also includes a thermocycler adapted to receive the microwell tape in a containment receptacle, the containment receptacle adapted to advance the microwell tape through a temperature program in the thermocycler. Finally, the system includes a detector adapted to analyze the contents of wells of the microwell tape, wherein the detector head is affixed to a transom such that the detector head can move in the X and Z axes and wherein the detector head is indexed to the microwell tape such that the detector head passes across the microwell tape in the X-axis and wherein the drive mechanism advances the tape along the Y-axis such that the detector head has access to the wells of the microwell tape.

The invention disclosed herein addresses the problems associated with the high-throughput screening of small-volume samples. By utilizing a submicroliter volume microwell tape, large numbers of small-volume samples can be prepared, reacted, analyzed and stored. By automating the process from the introduction of unique samples and addition of small volumes of reagents until final analysis, error inherent in human handling is avoided, resulting in rapid, consistent and repeatable analysis of small-volume samples in a high-throughput analysis.

The objects and advantages of the invention will appear more fully from the following detailed description of the preferred embodiment of the invention made in conjunction with the accompanying drawings.

DETAILED DESCRIPTION OF THE INVENTION

Figure 1:
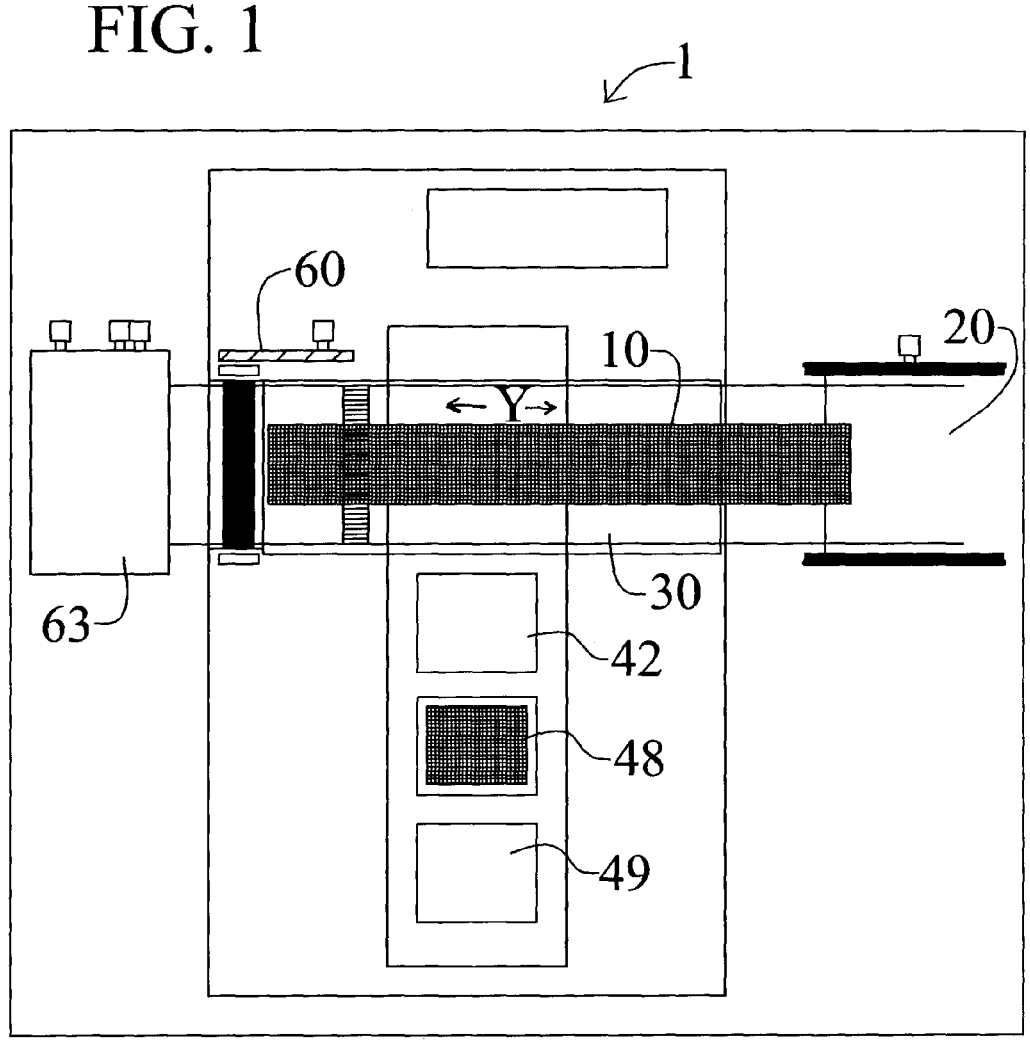
FIG. 1 is a schematic overhead diagram of the floor plan of the microwell assay system.

Referring now to the drawings and particularly to FIG. 1, the present invention is directed to a system 1 for the automatic processing of a large number of small-volume samples. The system is particularly adapted for use in detecting short tandem repeat polymorphisms (STRPs), SNPs and diallelic short insertion/deletion (indel) polymorphisms.

FIG. 1 illustrates a floor plan of system 1. System 1 is specifically designed for use with a microwell tape 10 having a continuous length along a Y-axis and containing a plurality of wells 12, illustrated in FIG. 2. The wells 12 are optimized to hold submicroliter volumes of samples for analysis.

System 1 includes a variety of components, including the following:

A. a drive mechanism 30 for advancing the tape 10 through the system 1;

B. a pipetter station 40 for transferring samples from the sample container to the tape 10;

C. a dispenser station 50 for transferring reagents to the microwell tape; and

D. a sealer station 60 for sealing a sealer tape to the microwell tape 10.

As will be seen later in the disclosure, the system may also include a thermocycler for receiving the microwell tape in a containment receptacle, and a detector for analyzing the contents of wells 12 of the microwell tape 10.

Microwell Tape

Figure 2:
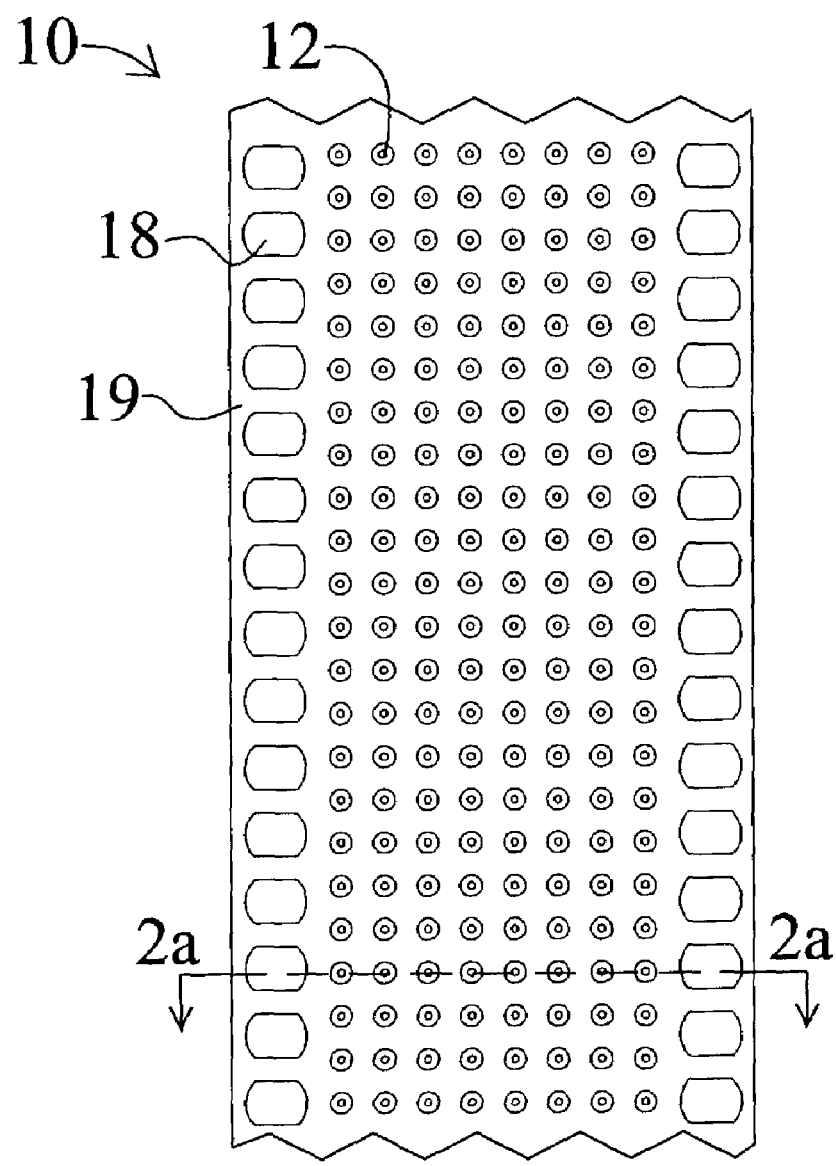
FIG. 2 is a top plan view of the microwell tape disclosed herein.
Figure 2A:
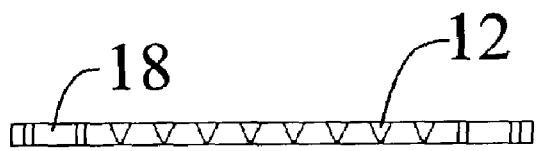
FIG. 2a is a cross-sectional view of FIG. 2 taken along lines 2a-2a of FIG. 2.
Figure 3:
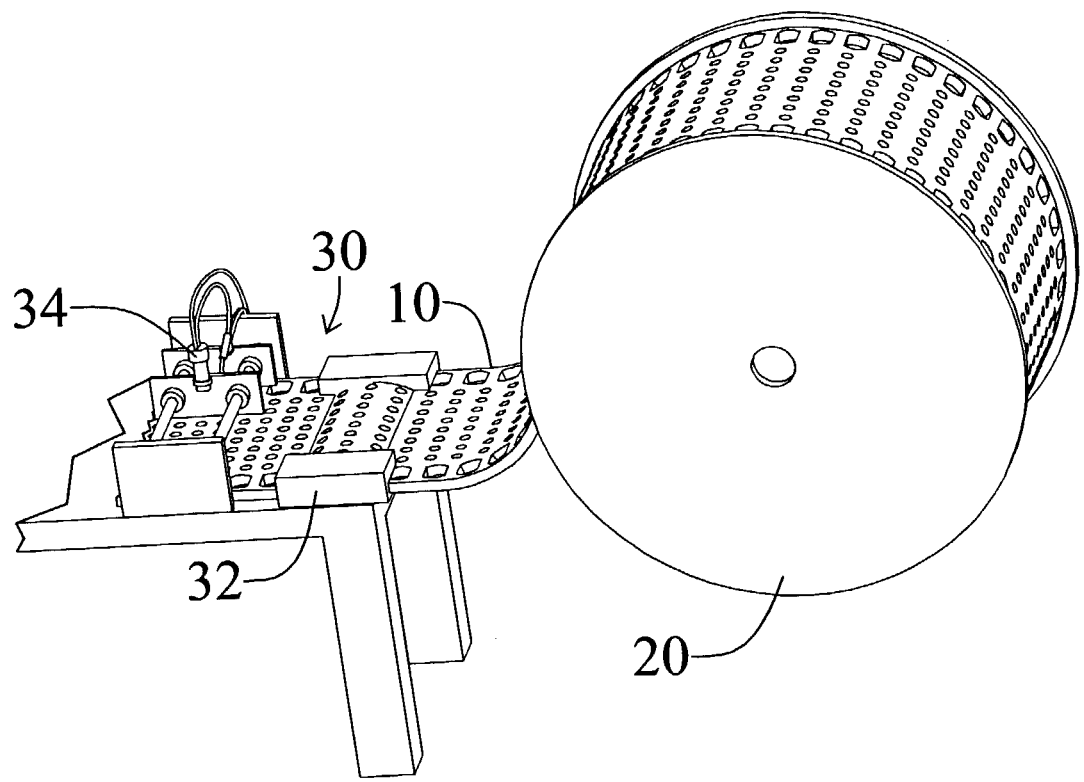
FIG. 3 is a perspective view of the microwell tape wound around a storage reel prior to entering the drive mechanism of the system of present invention.
Figure 4:
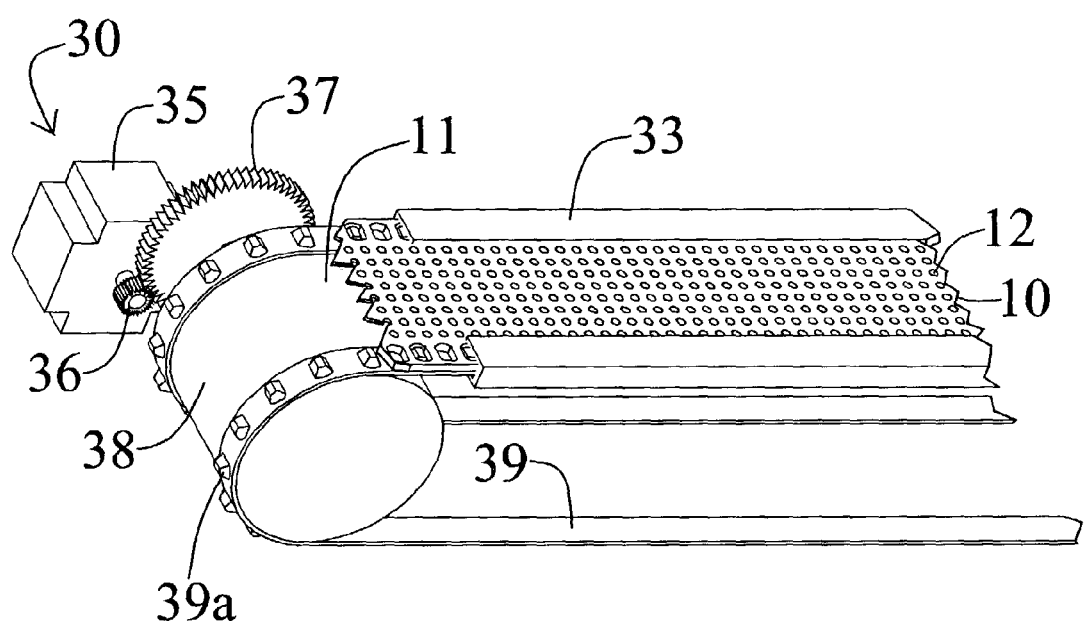
FIG. 4 is a perspective view of the microwell tape engaged with the drive mechanism.

The system 1 is designed to be used with a microwell tape 10 which allows for continuous analysis of samples. As illustrated in FIGS. 2, 2a and 3, the tape 10 is continuous and flexible. The tape 10 is designed to have indexing perforations 18 along the lateral margins 19 such that the tape 10 is driven through the analysis system at an optimum speed and does not require operator handling. The indexing perforations 18 are adapted to engage the pins 39a of a drive mechanism 30, as illustrated in FIG. 4, thus moving the tape 10 through the assay system 1. The tape 10 is made from a plastic polymer and may be embossed or heat molded from a plastic or a plastic polymer. In some embodiments, the tape 10 may be made from polycarbonate, polypropylene, silicone, polyethylene, polyurethane or the like. Preferably, the tape 10 is clear for reagent viewing or detecting.

The tape 10 is designed to include a plurality of conical flat bottom or "V" shaped wells 12 therein. This shape allows for the analysis of small reaction volumes ranging in size from greater than 1000 nl to less than 1 nl. In an exemplary version, the reaction volume in the well 12 is about 800 nl. In a more preferred embodiment, the well 12 is designed to hold a sample that has a volume of 200 nl. In a still more preferred embodiment, the reaction volume is about 25 nl.

Figure 2B:
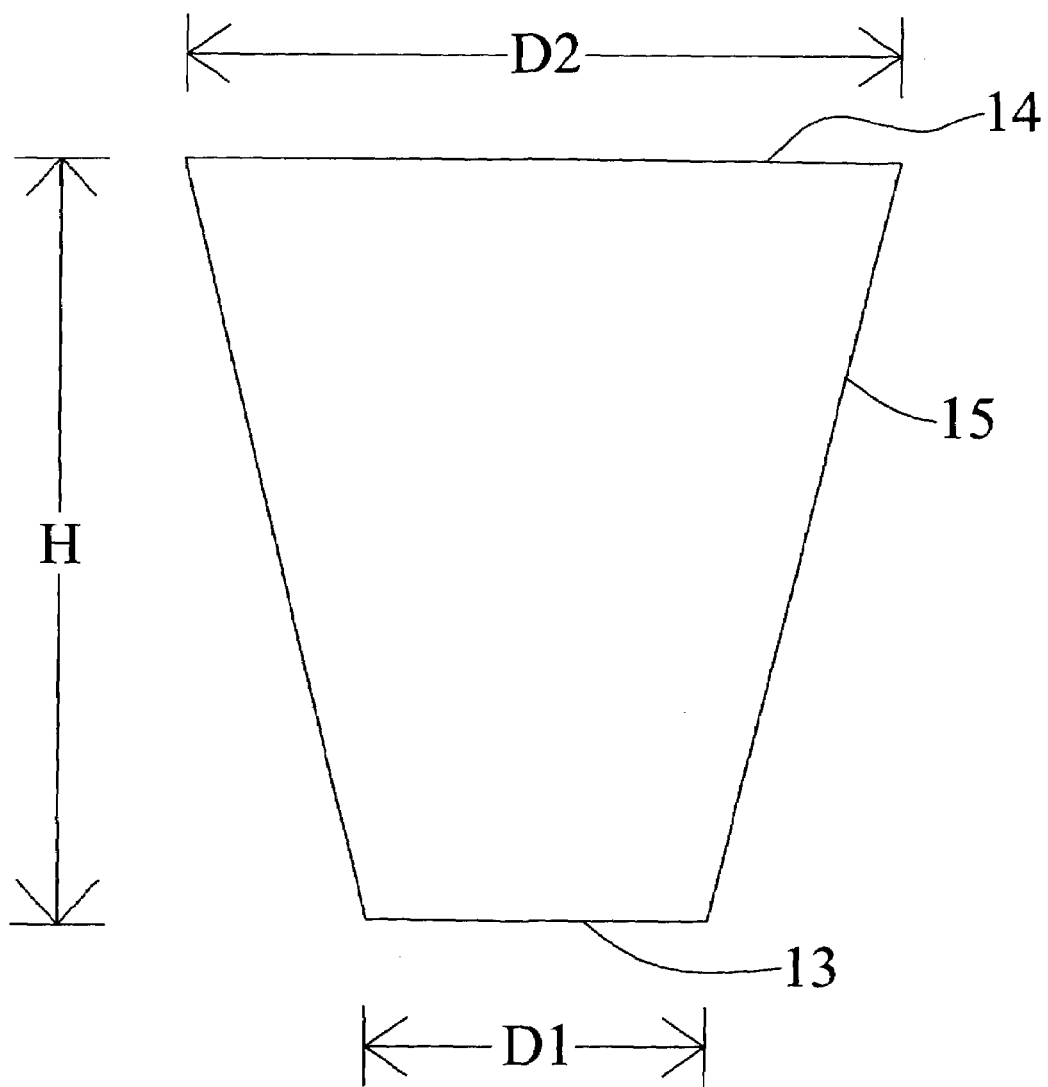
FIG. 2b is a cross-sectional view of one well of FIG. 2.

In order to allow the repeatable measurement of very small volumes, the wells 12 of the tape 10 are highly tapered "V"—or conical-shaped having a flattened base 13, an exposed opposite end 14 and a conical wall 15 defined by the diameter of the base 13 and end 14, as illustrated in FIG. 2b. The shape is defined by the height H, the diameter D1 of the base 13, and the diameter D2 of the top 14. This shape facilitates the collection and mixing of the well contents in the deepest and most narrow portion of the well 12, enhancing the repeatability of small-volume measurement. Further, the shape allows the introduction of the pin array tip 44 into the deepest portion of the well 12.

In addition, use of the microwell tape 10 facilitates the high-throughput screening of large numbers of samples due to its ease of handling, lack of need for stacking large numbers of microtiter plates and ease of storing. Further, a single roll of microwell tape 10 can substitute for over 500 384-well microtiter plates and over 2000 96-well plates. Thus, the sheer amount of space and money saved in utilizing the microwell tape is enormous.

Drive Mechanism 30

Referring now to FIGS. 3 and 4, the tape 10 may be stored on a storage reel 20. In use, the tape is fed into a pinned belt drive mechanism 30 by spring-loaded guide clips 32. The drive mechanism 30 also includes a solenoid valve 34, which has the function of dispensing small volumes by using pressure pulses as the valve is opened. As illustrated in FIGS. 3 and 4, the tape 10 with its small-volume microwells 12 and lateral indexing perforations 18 are clearly visible being fed into the guide clips 32 of the drive mechanism 30. While the drive mechanism 30 can be any such mechanism capable of moving the microwell tape 10 through the assay system, such as a sprocket wheel, in a favored embodiment, it is a belt pin drive as illustrated in FIG. 4.

Figure 5:
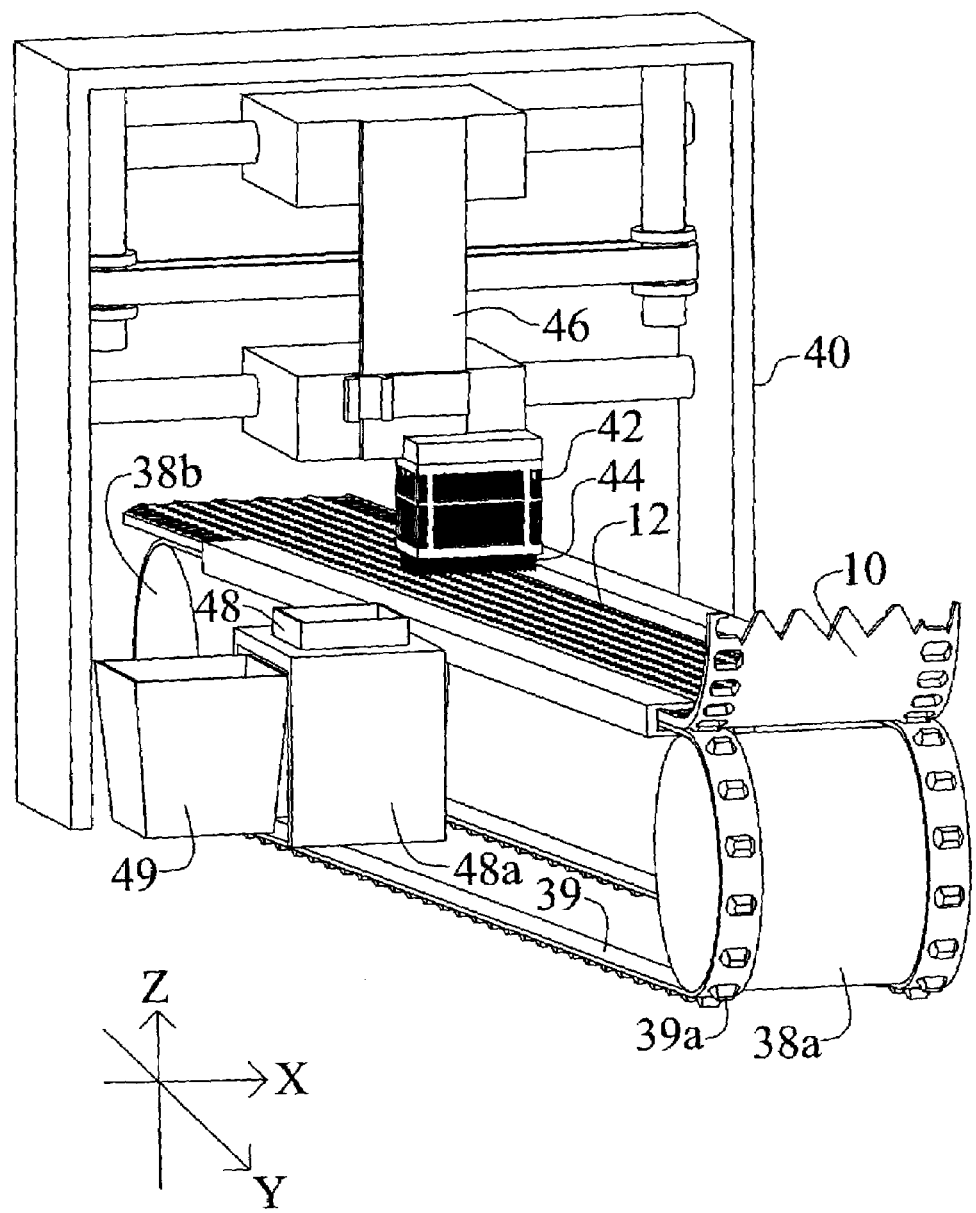
FIG. 5 is a perspective view of the microwell tape entering the pipetter station of the system of the present invention.

As further illustrated in FIGS. 4 and 5, the drive mechanism 30 includes a motor 35, having a drive cog 36 which engages a drum cog 37 which in turn drives a forward belt drum 38a. The forward belt drum 38a turns, moving two endless pin belts 39, one on each side of the belt drum 38. The pin belts 39 further include spaced indexing pins or nibs 39a to engage the tape indexing perforations 18 and, in turn, advance the tape 10 through the drive mechanism 30. Guide rails 33 position the tape 10 along the track. As illustrated in FIG. 4, the forward belt drum 38a engages the pin belts 39 which show the pins 39a protruding to engage the indexing perforations 18 of the microwell tape 10.

In operation, the pins 39a extend the length of the tape path marked by the guide rails 33. The drive mechanism 30 is situated near the end 11 of the tape 10 path. The forward belt drum 38a is positioned at one end of the tape path. As illustrated in FIG. 5, the rear belt drum 38b is positioned at the other end. Together, the belt drums 38a, 38b stretch the pin belts 39 giving them integrity to advance the tape 10. The pins 39a are affixed around the belt drum 38 such that the tape 10 is engaged to the pins 39a when the tape 10 enters the spring clips 32 and is held in an engaged position by the guide rails 33 throughout the tape path. In an exemplary version, only the rear belt drum 38b is driven by the motor 35 such that fine control of the motor 35 allows discrete movement of the microwell tape 10 through the tape path.

As disclosed, the mechanism for moving the tape 10 of the present invention has many advantages over other types of automated systems. As may be apparent to those of skill in the art, because the microwell tape 10 is driven by pins 39a of the pin belts 39 engaging with the indexing perforations 18 of the tape 10, the tape 10 is propelled entirely by its engagements with the drive belt 39. Therefore, the tape 10 can be moved in both a forward and a reverse direction as desired. Further, the belt drive mechanism 30 is designed and configured such that it can be advanced one row at a time, reversed one row at a time or moved in any multiple in either direction desired. Thus, while in one embodiment of the invention, it is conceived that the fewest units of use would be based on the method of introducing the largest plurality of unique samples, such as the 384 pin device described below, any smaller or larger unit of sampling device is amenable for use by the system disclosed herein.

Pipetter Station 40

Figure 6:
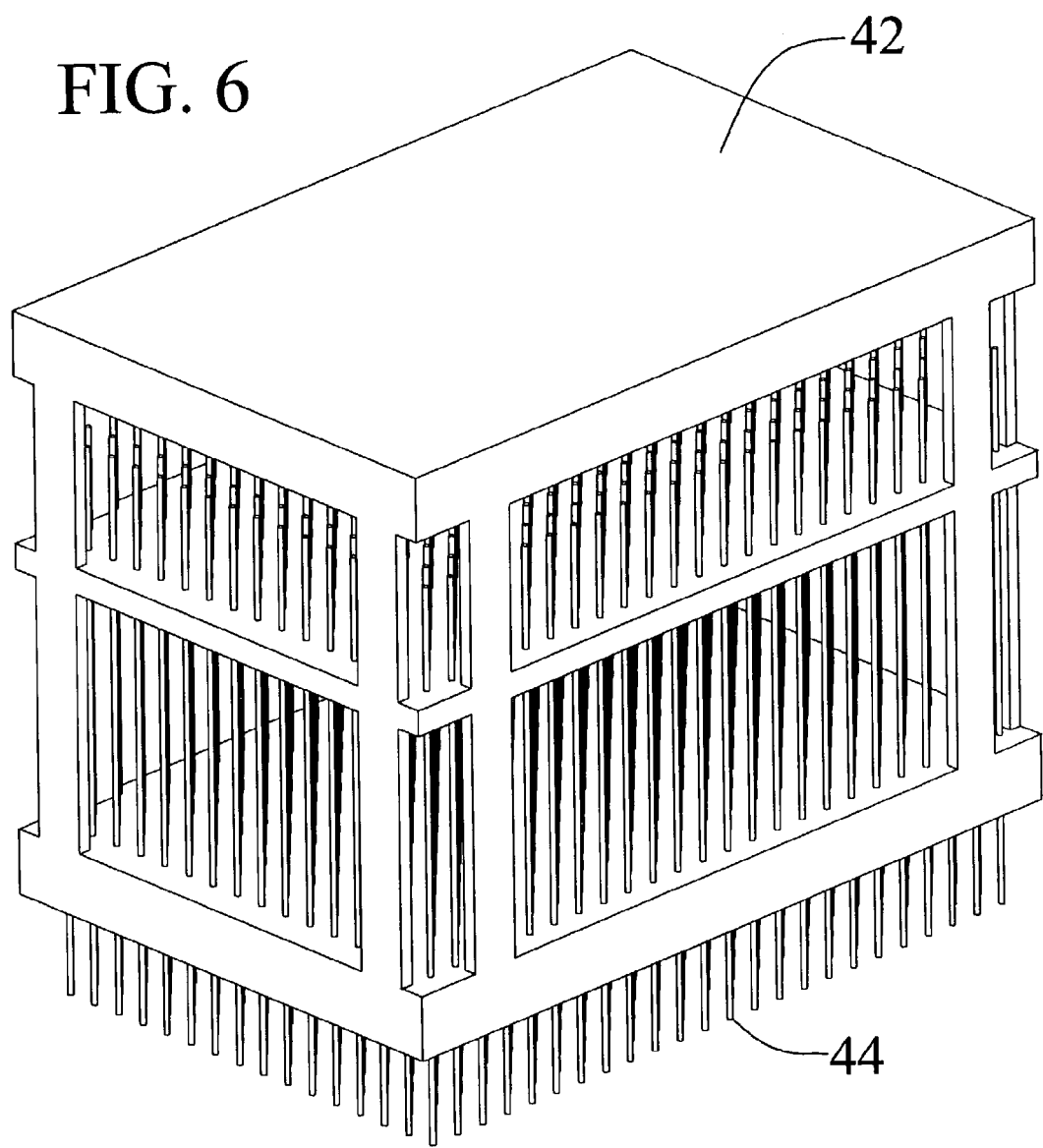
FIG. 6 is a perspective view of the 384 pin array pipetter of FIG. 5.

As illustrated in FIG. 5, the pipetter station 40 comprises a pipetter pin array 42 for dispensing submicroliter volumes of sample into the wells 12 of the microwell tape 10. In one preferred embodiment, the sample pipetter pin array 42 is not a positive displacement pipetter but rather a "pin" system, illustrated in FIG. 6 comprising a multitude of pins 44 whereby samples are transferred from a microtiter plate 48, illustrated in FIG. 5 on a stand 48a, to the wells 12 of the tape 10 by surface tension to the pins 44. It is a further aspect of the invention that the pins 44 are in the form of a 384-pin array as illustrated by pipetter pin array 42 in FIG. 6. This arrangement facilitates the transfer of samples from a 384-well microtiter plate 48 directly into the wells 12 of the tape 10. However, those of skill in the art will appreciate that if microtiter plates with fewer or more wells are used, a complementary pin array could be used. For example, if a 96-well plate is used, then a 96-pin array would be used, or if a 1536 well plate is used, then a 1536 pin array would be used. Also, non-standard spacing could be used.

In one exemplary version of the invention, the pipetter pin array 42 may comprise a positive displacement pipetter. Positive displacement pipetters are commercially available and known to the art. For instance, TOMTEC, Hamden, Conn., produces the 384 tip array Quadra 3 positive displacement pipetter. As produced, the pin array 42 is typically designed to sample microtiter plates wherein the tip array remains stationary and the microtiter plate is mechanically brought to the tip array. The inventors have found that the pipetter pin array 42 can be adapted for use on the microwell tape 10 as the tape 10 engages the drive mechanism 30 such that automation of the analysis system is not interrupted.

In yet another exemplary version, the pipetter pin array 42 is a passive displacement pipetter comprising passive transfer pins 44 which transfer the sample by passive means. In this embodiment the pins 44, transfer a nucleic acid solution based on surface tension of the solution adhering to the pins 44. The passive transfer pin head was adapted from the 384 pin transfer device commercially available from V&P Scientific, San Diego, Calif. While the use of passive transfer pin arrays is known in related art for use in culturing bacterial colonies, for example (See U.S. Patent application 20020013958 to Lalgudi et al., the disclosure of which is incorporated herein by reference as it relates to the pin array), the pins are routinely used to transfer submicroliters to glass slides for microarraying.

When the embodiment of the invention comprises the passive transfer pin array, moving parts are greatly reduced and error becomes a function of the adhesion of the sample. As may be appreciated, the passive transfer pin array reduces error inherent in moving parts by using surface tension to adhere the sample to the pin 44 and transfer the sample to the wells 12 of the tape 10. By using surface tension to transfer the unique sample, submicroliter volumes of about as low as 1 nl of sample can be repeatably transferred.

In operation, as illustrated in FIG. 5, the pipetter pin array 42 is suspended from a transom 46. Defining the Y-axis as the axis of the length of the continuous microwell tape 10, the pipetter pin array 42 translates on the transom in the X-axis and the Z-axis.

Illustrated in FIG. 5, microtiter plates 48 are arranged at the side of the microwell tape 10 such that the plates 48 are stationed directly in the axis of movement as the pipetter pin array 42 translates along the X-axis of the microwell tape 10. Adjacent to the microtiter plates 48, on the side opposite from the microwell tape 10, is situated a flow bath 49. Flow baths such as that disclosed are commercially available from, for instance, TOMTEC. The flow bath 49 comprises a reservoir dimensioned and configured to accept the pipetter pin array 42. The flow bath 49 has a constant flow of clean deionized water which can also be subjected to an ultrasonic action. Thus, after transferring the sample to the microwell tape 10, the pipetter pin array 42 is lifted, translocated over the flow bath 49 and lowered into the bath 49 for a sufficient time or number of cycles to remove the previous sample. Situating the microtiter plate 48 and the flow bath 49 on the X-axis of the microwell tape 10 allows the pipetter pin array 42 to access these three components by translation across the transom 46 in the horizontal direction and translation along the Z-axis. It will be appreciated that, while in a preferred embodiment the microtiter plates 48 are positioned between the flow bath 49 and the microwell tape 10, the positions are relative and may be reversed in other embodiments.

In an exemplary version of the present invention, the pipetter pin array 42 translates across the X-axis of the tape 10 and the pipetter pin array 42 and descends into the wells of a 384-well microtiter plate 48. The wells of the microtiter plates 48 contain the unique sample. When the sample being assayed is a nucleic acid sample, the nucleic acid may be dried in the well 12 of microwell tape 10 and then resuspended in a mix comprising assay reagents. The pipetter pin array 42 takes an appropriate aliquot of the samples in the wells of the microtiter plate 48. The pipetter pin array 42 is then raised on the transom 46 and translocated across the X-axis, such that it is directly over the microwell tape 10. The pipetter pin array 42 is then lowered until it accesses the microwells 12 of the tape 10 and aliquots of the sample are delivered to the wells 12 of the microwell tape 10. Upon contact with the wells 12 of the microwell tape 10, surface tension adheres the sample to the wells 12 of the microwell tape 10, and the pipetter pin array 42 is raised from the surface of the microwell tape 10. The flow bath 49 is positioned outside of the microtiter plates 48 on the X-axis of the microwell tape 10, and the pipetter pin array 42 translates until it is suspended over the flow bath 49 whereupon the pipetter pin array 42 is lowered until the pin tips 44 are suspended in the flow bath 49 and the pins 44 are cleaned by the flow of water coupled with ultrasonic action. Upon cleaning of the pins 44 of the pipetter pin array 42, the pipetter pin array 42 is ready to sample the next plate.

Because of the fine control by which the microwell tape 10 is moved along its Y-axis by the pinned drive belt 39, the pipetter pin array 42 has only to move in two axes, X and Z. For movement of the pipetter pin array 42 in the X-axis, the pipetter pin array 42 is connected to the transom 46 which is suspended above the microwell tape 10. The transom 46 is designed and configured such that a belt and drive mechanism translates the pipetter pin array 42 along the X-axis to a site directly over the tape 10 and to a site directly over the sample plates 48 being assayed.

Dispenser Station 50

The system 1 also comprises a dispenser station 50 suitable for dispensing submicroliter volumes of common reagents into the wells 12 of the microwell tape 10. The dispenser station 50 includes a dispenser 52, which resembles an ink jet dispenser, optimized to inject appropriate volumes of common reagents into the wells 12 of the microwell tape 10 where the total reaction volume may range between 1 nl and 1000 nl.

Figure 7:
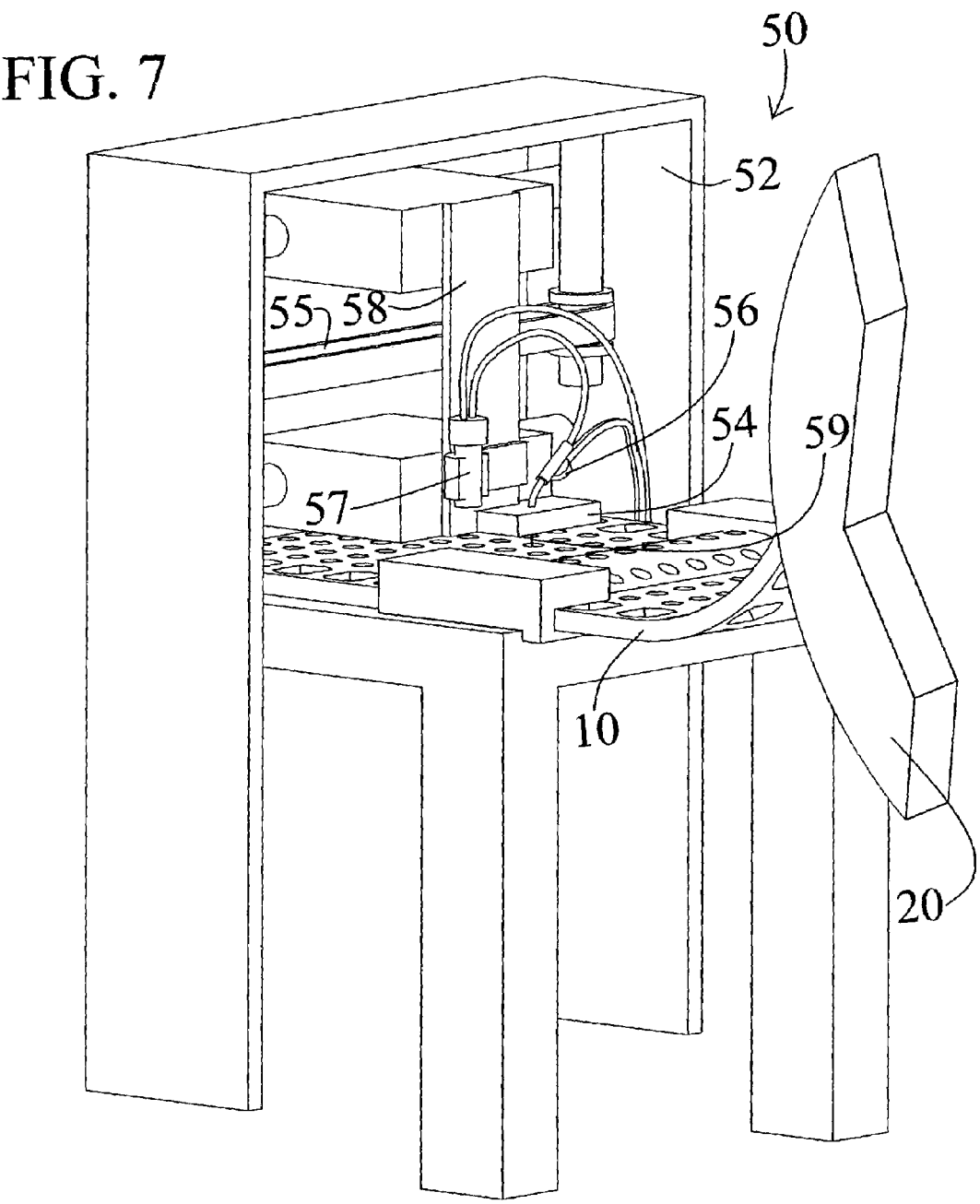
FIG. 7 is a perspective view of the dispenser station of the system of the present invention

FIG. 7 illustrates the reagent dispenser 52 comprising a dispenser head 54 having a solenoid valve 56 similar to an inkjet printer and being fixed to a dispenser transom 58 similar to the pipetter pin array 42. The dispenser head 54 has an injection needle 59. By being connected to a common reservoir 57 of reagents or master mix, a single solenoid valve 56 can rapidly and accurately translate across the microwell tape 10 in the X-axis, accurately dispensing volumes as low as about 20 nl in each well 12 of the tape 10. Similar submicroliter volume dispensers are commercially available. For instance, Innovadyne (Santa Rosa Calif.) produces a NANOFILL 8 unit having a dispensing volume of as low as 100 nl, while Cartesian Technologies (Irvine, Calif.) produces the SYNQUAD system dispensing a reproducible volume of 50 nl.

As described for the pipetter pin array 42, the dispenser head 54 is moved across the tape 10 by the use of a transom 58 and a motor driven belt 55. While in one embodiment the dispenser 52 comprises a reservoir 57, in an alternative preferred embodiment, the reservoir 57, containing the reagents or master mix, is not located on the dispenser transom 58 but is extraneous and is situated to the side of the dispenser 52. The dispenser head 54 then translates to the extraneous reservoir or microtiter plate (not shown) and the injection needle 59 aspirates the reagent. The dispenser head 54, then returns to the tape 10 and dispenses reagent to the wells 12 accordingly. Upon depletion of the reagent, the dispenser head 54 moves to a wash station. The dispenser head then returns to the extraneous reservoir (not shown) and aspirates a further quantity of reagent.

Sealer Station 60

Figure 8:
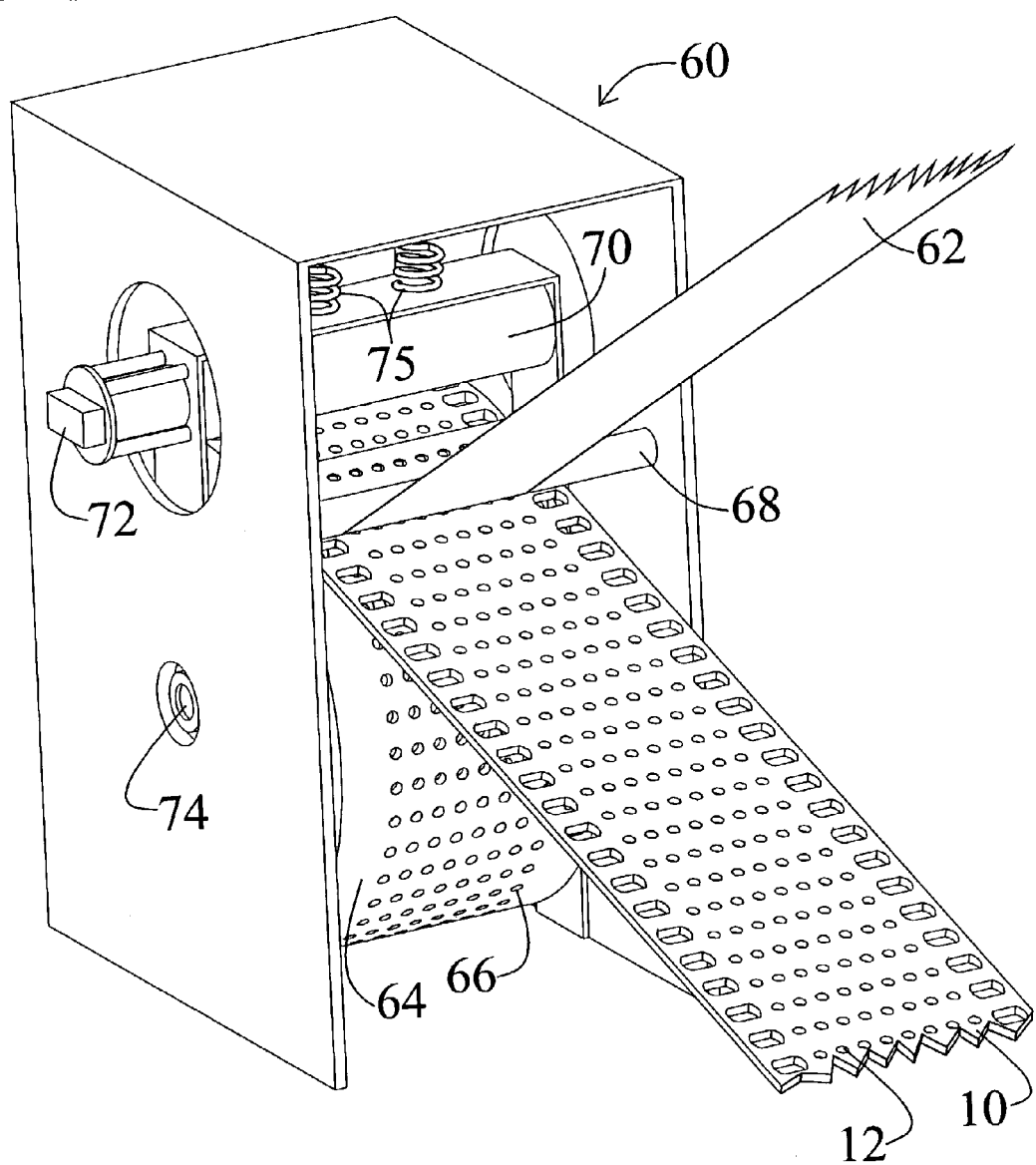
FIG. 8 is a perspective view of the sealer station of the system of the present invention.

Referring now to FIG. 8, the system 1 comprises a method of sealing the microwell tape 10 such that the contents inside are not contaminated. In a preferred embodiment, the microwell tape 10 proceeds from the dispenser station 50 to the sealing station 60 unit where sealing tape 62 is overlain the microwell tape 10 and seals the wells 12 of the microwell tape 10. In a preferred embodiment, the sealing tape 62 is sealed using a heat and/or pressure sealing system. However, other methods of sealing the microwells of the microwell tape, for instance adhesives, may be used, the only caveat being that contamination of the contents of the microwells must be avoided and the contents left undisturbed.

After the wells 12 of the microwell tape 10 have been filled with the unique sample by the pipetter pin array 42 and the reagent mix by the reagent dispenser 52, the microwell tape 10 is then sealed with a sealer tape 62. The sealer tape 62 eliminates risk of contamination and also allows the reactions in the wells to be stored for long periods or submerged in water. The sealer tape 62 comprises a planar tape made from a similar material as the microwell tape 10 and is stored on a storage reel 63 as shown in FIG. 1. Preferably, the sealer tape 62 is clear for reagent viewing or detecting. The sealer station 60 is uniquely designed to provide a method for tape uptake and simultaneous sealing. Upon introduction of the reaction components to the wells 12, the open side of the microwell tape 10 is juxtaposed to the sealer tape 62. The juxtaposed tapes 10, 62 are then introduced into the sealer station 60. As illustrated, the sealer station 60 works similarly to a wringer of an old fashioned washing machine. A large bottom indexing drum 64 has cavities 66 dimensioned and configured to be in register with the wells 12 of the microwell tape 10. The sealer station 60 is further comprised of a wrap bar 68 and a heat drum 70 heated by a heating element 72. The microwell tape 10 and the sealing tape 62 enter the sealing device 60 under a wrap bar 68. While the pin belt 39 could drive the microwell tape through the sealer station 60, in a particularly favored embodiment the tape 10 is driven through the sealing mechanism by the indexing drum 64 itself, which is rotated on its axis 74 by a motor. In this embodiment, the bottom profiles of the wells 12 of the microwell tape 10 are taken up by the cavities 66 of the indexing drum 64. The heat drum 70 is situated directly on top of the indexing drum 64 and is under tension by means of springs 75. As the sealing tape 62 and the microwell tape 10 move past the heat drum 70, the sealing tape 62 is "ironed" or pressed onto the microwell tape 10. Once the microwell tape 10 is sealed, the microwell tape 10 can be wound around a storage reel 20 as illustrated in FIG. 3 and stored, or the tape can be directed to further manipulations.

This unique design of the sealer station 60 provides several benefits. First, the contents of the wells 12 are protected from mechanical stress and also heat stress. Second, the progress of the microwell tape 10 through the sealer station 60 is driven directly by the microwells 12 passing through the device. Thus, there are no intervening mechanisms which would allow the tape 10 or the indexing drum 64 to get out of register. Further, the disclosed arrangement allows tension to be placed on the sealing tape 62 and microwell tape 10 that is held by the wrap bar 68, thereby eliminating air bubbles and insuring a comprehensive seal.

Thermocycler Station 80

The system can also comprise a thermocycler station 80 adapted to contain the microwell tape 10 and designed such that the cycling times required for carrying out a PCR reaction are minimized. In a preferred embodiment, the thermocycler station 80 is a waterbath thermocycler having three separate reservoirs 82, 84, 86. The reservoirs 82, 84, 86 are adapted to provide optimum temperatures for annealing primers to sample nucleic acid, elongation of the primers and melting of the complementary strands so the cycle may be repeated.

Depending on the sample type and the incubation required of the microwell contents, the microwell tape 10 can be cared for as needed. When the contents comprise a PCR reaction or other biological reaction requiring temperature dependent incubation, the microwell tape 10 can be cared for appropriately. If the contents are to be stored, the tape 10 can be wound on the storage reel 20 and conveniently stored in a low temperature environment.

Figure 9:
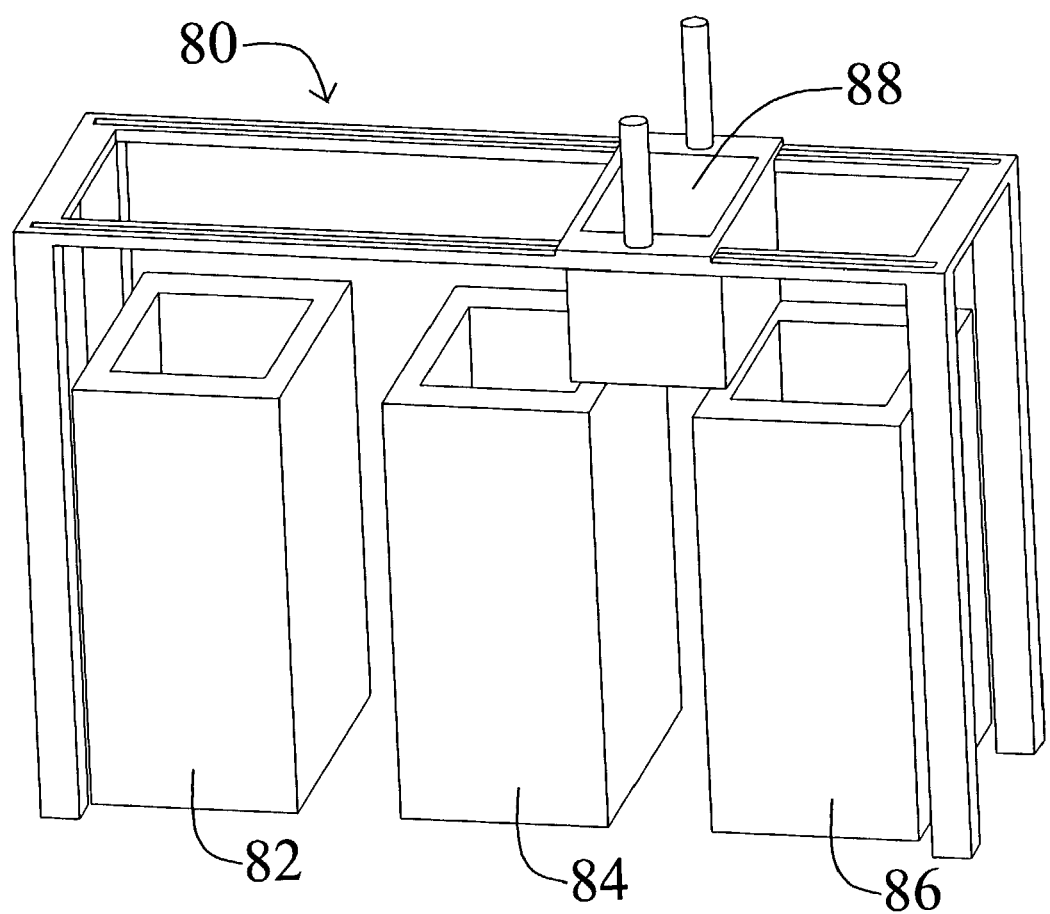
FIG. 9 is a perspective view of the waterbath thermocycler illustrating individual thermal units.

When the contents of the microwell tape 10 comprise a PCR reaction, the tape 10 is directed to the thermocycler station 80. While in one embodiment, the tape 10 may be taken up from the sealing device 60 and wound around a storage reel, in other embodiments the tape 10 is immediately subjected to a reaction protocol. For PCR reactions, the microwell tape 10 is directed to the thermocycler station 80. While in some embodiments, the thermocycler may be a dry thermocycler, in a preferred embodiment, the thermocycler is a waterbath thermocycler 80 as shown in FIG. 9. In this embodiment, the thermocycler station 80 is optimized to eliminate ramping time between temperatures by comprising three separate water reservoirs 82, 84, 86, each having the appropriate temperature for the annealing, elongation and separating steps of the PCR reaction. In a preferred embodiment, the reservoirs 82, 84, 86 each have a two panel cover (not shown) similar to swinging doors, fixed over the reservoir opening by springs (not shown) such that the temperature of each reservoir is maintained. In operation, a containment receptacle 88, containing the microwell tape 10 is lowered and submerged in the reservoir. Upon removal, the receptacle 88 is lifted up and the receptacle is translocated to the next reservoir. The tape 10 is placed in the containment receptacle 88 which is automated such that after the microwell tape 10 has been incubated for the appropriate period of time in each of the required temperature environments, the containment receptacle 88 is raised by means of an automated rack and pinion (not shown) and translocated to the appropriate bath where the receptacle 88 is lowered, allowing the reactions to incubate for the appropriate period. After incubation, the receptacle 88 is raised and translated to the next reservoir. This process can continue until the appropriate number of cycles has been completed for proper amplification of the PCR product.

In another embodiment, the thermocycler will be a dry thermocycler designed to have a rotary axis similar to an oven rotisserie unit such that, as the thermocycler progresses through its program, the tape is slowly rotated such that centrifugal forces keep the reaction mixed and the contents directed toward the bottom of the well. In addition, such a design allows for minimal ramping time during thermal cycles, facilitating the elongation and amplification of the PCR reaction. Dry thermocyclers are well known to the art. A representative example of a dry thermocycler is found in U.S. Pat. No. 5,602,756 to Atwood et al., which is incorporated herein by reference for a description of the dry thermocycler.

Detector Station 90

Figure 10:
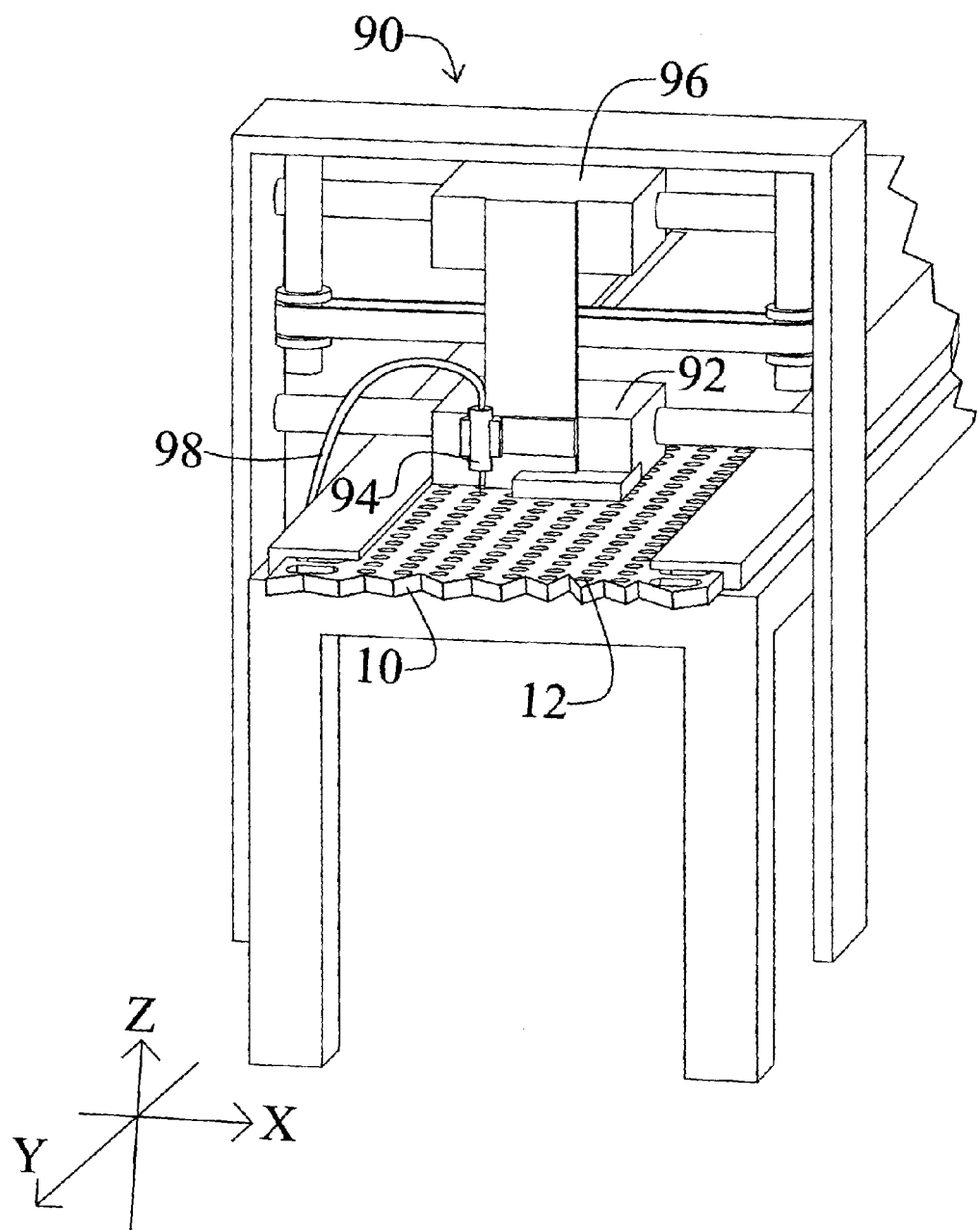
FIG. 10 is a perspective view of the detector station of the system of the present invention.

Illustrated in FIG. 10, the system 1 can also include a detector station 90. Detector systems are well known to the art. A representative system is described here. The detector station 90 includes a detector 92 optimized to read the contents of microwell tape 10. In a preferred embodiment, the detector 92 is a fluorescence detector. However, the detector 92 may be any detector capable of quantifying the analytic substrate contents of the microwell tape. Such detectors may comprise detectors, photomultiplier tube detectors and spectrophotometric detectors.

For analysis of the samples, the now-sealed microwell tape 10 can either be fed into the detector 92 following completion of sample thermocycle reactions or directed there immediately from the sealing station 60. While the detector 92 can be any type of detector known to the art for achieving the desired purpose, including a UV detector, a fluorescence detector, an IR detector, a charge-coupled device (CCD) detector or a spectrophotometer, all well-known to the art in a favored embodiment, the preferred detector is a fluorescence detector. When the detector is a fluorescence detector, it is a scanning fluorescence detector developed by Marshfield Clinic for genotyping work.

Referring now to FIG. 10, the detector head 94 is suspended on a transom 96 similar to the pipetter pin array 42 and dispenser 52 such that the detector head 94 can move across the tape 10 along its X-axis. In a particularly favored embodiment, the detector comprises a laser which is located in the detector body (not shown). The light comprising the activation energy travels via an optical fiber 98 to the detector head 94. A dichroic mirror (not shown) within the detector head 94 reflects the excitation energy into the wells 12 of the microwell tape 10 through an objective lens (not shown). The emitted energy is returned to the detector head 94 through the objective lens (not shown) and travels to the body of the detector 92 through a separate optical fiber (not shown). The quantification of the fluorescence energy is then made via computer programs which determine the intensity of the emitted energy. When the fluorophors emit different wavelengths or fluoresce at different colors, the computer program integrates the different emitted energies, computing a ratio and thus determining the presence of homozygous or heterozygous alleles of substitution or indel polymorphism.

The information derived from the detector is fed into a computer interface whereby the output of the detector is compiled and integrated to determine the concentration of substrate in the wells of the microwell tape.

The operation of the system 1 will be described with reference to FIG. 1. Referring to FIG. 1, the floor plan of the system 1 of instant invention can be seen. The unused tape 10 is stored on storage reel 20. Upon activating the drive mechanism 30, the tape 10 is passed to the pipetter station 40 which includes the pipetter pin array 42, microtiter plate 48, and flow bath 49. It is also within the scope of the present invention to include an identification system, such as a bar code identifier, at this position. Once the sample is applied to each well 12 of the tape 10, as described above, the tape 10 then passes through the sealing device 60, sealing the tape 10 before the tape 10 is wound and taken onto the storage reel 63. In the embodiment described thus, the tape 10 can then be stored or immediately advanced to the detector station 90, described above. In addition, while the step of placing the reagents in the wells 12 before the DNA is recited, those of skill in the art will understand that the step of adding the DNA may be performed prior to or after that of adding the reagents.

Control of the system is effected by software. The software is designed such that the movement of the pipetter pin array 42, dispenser 52 and detector 92 are indexed and in register with the wells 12 of the microwell tape 10. In a preferred embodiment, the software also is capable of tracking the contents of the microwells and correlating the contents with the results of the fluorescence analysis. In addition, there is a software interface code for PC user intervention should additions or adjustments to the system be necessary.

In a further embodiment, bar codes are added to the microwell tape, denoting the contents of the wells such that the microwell tape or an individual well can be scanned to determine the results of the analysis.

Using the system described, rapid analysis of a large number of small-volume samples may be effected. In an exemplary version of the invention, the samples will comprise a PCR reaction in which specific primers for genomic polymorphisms are used. In a particularly favored embodiment, there are three primers. One primer is 5' to the polymorphic region and is not labeled. The other two primers are 3' and within the polymorphic region and are specific for one of two variant alleles. Each of the specific primers is labeled with a different fluorophor such that visualization of the particular fluorophor incorporated into the PCR product is easily made. In an exemplary version, the fluorophors are fluorescein, which emits a green fluorescence, and "Joe" which emits in a green/yellow fluorescence. Further, the primers are constructed such that in their native form, they form a hairpin loop, bringing a quenching molecule within vicinity of the fluorophor. Thus, if a homologous sequence of the polymorphic region is present, the primer will anneal and the hairpin will be broken, taking the quencher away from the fluorophor and allowing fluorescence at the emitted wavelength. Absence of a homologous sequence for binding will not result in annealing of the primer and will not result in fluorescence. Thus, genomic polymorphisms that are homozygous for one or other alleles will fluoresce at either green/yellow or green wavelengths. If the DNA is heterozygous for the polymorphism, there will be a fluorescence of both green/yellow and green wavelengths but at an intensity less than the homozygous fluorescence.

While it is conceived that the disclosed devices and system are appropriate for use with any detector system which requires high-throughput screening and including detection methods requiring detection of UV energy, infrared energy, spectral analysis or other detection methods, it is a favored embodiment that the system and devices described herein can be used for fluorescence analysis of insertion/deletion or single nucleotide polymorphism in genetic analysis.

The invention will now be illustrated by the following example, which is exemplary in nature and not intended to be restrictive.

EXAMPLE

Example 1

Detection of Insertion/Deletion Polymorphism or Substitution using PCR

1. DNA is prepared to a concentration of 6.25 ng/uL and is placed in a 384-microtiter plate.
2. A master mix is prepared comprising: PCR buffer, MgCl2, dNTPs, allele specific primer, common primer, AMPLIFLUOR UNIPRIMER FAM and AMPLIFLUOR UNIPRIMER JOE (Seroligicals Corporation, 5655 Spalding Drive, Norcross, Ga. 30092), Taq (preferred PLATINUM TAQ, Invitrogen Life Technologies, 1600 Faraday Avenue, Carlsbad, Calif. 92008), and filtered sterilized water. The master mix is placed in a 96 deep well microtiter plate.
3. The plate containing the DNA is placed in the "pin array" access area.
4. The microwell tape is fed into the uptake guide.
5. The 384 array pipetter accesses the microtiter plate and takes a 800 nl sample of each well of the microtiter plate with a leading air gap.
6. The pin array is translated by means of the transom to the microwell tape. The pin array descends and the array ejects 800 nl of DNA sample and air gap, depositing the DNA. The DNA is then dried to the bottom of the well.
7. The tape progresses to the dispenser area for the addition of common reagents (master mix) where the DNA is resuspended, bringing the total volume of the reaction to 800 nl.
8. The tape is introduced into the sealing unit where the sealing tape is applied.
9. The tape is then deposited in the waterbath thermocycler.

The protocol for the thermocycler is:
First step:
   95° C. for 60 seconds
Followed by cycling:
   95° C. for 20 seconds;
   55° C. for 40 seconds;
   72° C. for 20 seconds;
The cycle is repeated 33 times, for a total of 75 minutes
Followed by a final extension:
   72° C. for 6 minutes
The cycle is repeated 33 times, for a total of 75 minutes followed by a final extension.

10. The contents of the tape are allowed to come to temperature, and moisture collected on the walls of the wells is allowed to condense and spun to the bottom of the well by rotation of the tape as previously described.
11. The microwell tape is then fed into the detector and taken up by the pin belt drive mechanism 30 where the tape passes under the detector head. Results of the positive controls show: homozygous long, homozygous short, heterozygous, and negative control samples.

As will be apparent to one of skill in the art, in a preferred embodiment, the disclosed invention is directed to the high-number, low-volume, diallelic insertion/deletion (indel) or substitution polymorphism genotyping. However, the devices used and sequences taught can be utilized for many other assay systems requiring high-throughput analysis. In addition, while in one exemplary version of the invention, the DNA is placed in the microwells before the master mix, it is understood that in another version of the invention, the master mix may be placed in the well followed by the DNA sample.

It is understood that the invention is not confined to the particular construction and arrangement of parts herein illustrated and described, but embraces such modified forms thereof as come within the scope of the following claims.

What is claimed is:

1. A system for automatically analyzing a large number of small-volume samples, comprising:
   a. a microwell tape having a continuous length and containing a plurality of wells, the tape having first and second lateral edges defined by a continuous row of indexing perforations;
   b. a drive mechanism adapted to move the microwell tape through the system;
   c. a pipetter for transferring samples to the wells of the microwell tape;
   d. a dispenser for transferring a reagent to the well of the microwell tape;
   e. sealing means for sealing the wells of the microwell tape, wherein the sealing means comprises an indexing drum having cavities dimensioned to resister with the wells of the microwell tape;
   f. a thermocycler; and
   g. a detector for analyzing the contents of wells of the microwell tape.

2. The system of claim 1 wherein the drive mechanism comprises a pinned drive belt, the pinned drive belt being driven by a motor, wherein the pinned drive belt has pins regularly spaced along its length and wherein the pins are dimensioned and configured to matingly engage the indexing perforations of the microwell tape.

3. The system of claim 1 wherein the pipetter comprises a pin array comprising a plurality of pins, wherein the pipetter is further affixed to a transom such that the pipetter can move in an indexed manner to transfer samples to the microwell tape.

4. The system of claim 1 wherein the pipetter is a positive displacement pipetter.

5. The system of claim 1 wherein the pipetter is a passive displacement pipetter comprising a passive transfer pin array.

6. The system of claim 1 wherein the sealing means comprises a sealing tape.

7. The system of claim 6 wherein the sealing tape is stored on a storage reel.

8. The system of claim 7 wherein the sealing tape is clear for reagent viewing or detecting.

9. The system of claim 1 wherein the dispenser comprises a solenoid valve adapted to dispense submicro liter volumes of reagents, wherein the dispenser is affixed to a transom for moving the dispenser in an indexed manner to transfer samples to the microwell tape.

10. The system of claim 1 wherein the detector comprises a detector head affixed to a transom such that the detector head is indexed to the microwell tape such that the detector head passes over the microwell tape.

11. The system of claim 1 adapted for use in detecting short tandem repeat polymorphisms (STRPs), SNPs and diallelic short insertion/deletion (indel) polymorphisms.

12. The system of claim 1, wherein said sealing means comprises means for sealing the tape using a heat or pressure sealing system.

13. The system of claim 1, wherein said sealing means further comprises:
   i. a sealing tape;
   ii. a wrap bar to position the sealing tape; and
   iii. a heat drum heated by a heating element to seal the sealing tape to the microwell tape.

14. The system of claim 1, wherein said sealing means further comprises:
   i. a sealer tape, and
   ii. a heat drum, wherein the heat drum is under tension and juxtaposed to the indexing drum.

15. A system for automatically analyzing a large number of small-volume samples comprising:
   a. a microwell tape having a continuous length and containing a plurality of wells, the tape having first and second lateral edges defined by a continuous row of indexing perforations;
   b. a drive mechanism adapted to move the microwell tape through the system;
   c. a pipetter for transferring samples to the wells of the microwell tape;
   d. a dispenser for transferring a reagent to the well of the microwell tape;
   e. sealing means for sealing the wells of the microwell tape, wherein the sealing means comprises an indexing drum having a plurality of cavities in register and dimensioned and configured to reflect profiles of the wells of the microwell tape;
   f. a thermocycler; and
   g. a detector for analyzing the contents of wells of the microwell tape.

16. The system of claim 15, wherein said sealing means further comprises a sealer tape, and a heat drum, wherein the heat drum is under tension and juxtaposed to the indexing drum.

17. The system of claim 16, wherein the sealer tape is stored on a storage reel.

18. The system of claim 17, wherein the sealer tape is clear for reagent viewing or detecting.

19. A sample characterization system utilizing a microwell tape for analysis of samples comprising:
   a. a microwell tape having a continuous length and containing a plurality of wells, the tape having first and second lateral edges defined by a continuous row of indexing perforations
   b. a drive mechanism adapted to automatically advance the microwell tape;
   c. at least one dispenser for dispensing reagents into the wells of the microwell tape; and
   d. sealing means for sealing the wells of the microwell tape, wherein the sealing means comprises an indexing drum having cavities dimensioned to register with the wells of the microwell tape
   e. a detector for analyzing the contents of wells of the microwell tape.

20. The system of claim 19 further comprising a thermocycler.

21. The system of claim 19 further comprising a detector for analyzing the contents of the wells of the microwell tape, wherein the detector comprises means to advance the microwell tape through the detector.

22. The system of claim 19 further comprising an identification station for identifying each sample.

23. The system of claim 22, wherein the identification station is a bar code station.

24. The system of claim 19, wherein the microwell tape comprises a plurality of wells, wherein each well has a sample volume ranging from 1 nanoliter to 1000 nanoliters.

25. The system of claim 19, wherein the microwell tape comprises a plurality of wells, wherein each well has a sample volume no greater than about 500 nanoliters.

26. The system of claim 19, wherein the microwell tape comprises a plurality of wells, wherein each well has a sample volume no greater than about 50 nanoliters.

27. The system of claim 19, wherein the dispenser comprises an array of positive displacement heads for depositing sample aliquots in the wells of the microwell tape for analysis, a pin transfer system and a solenoid valve.

28. The system of claim 19, wherein each well of the plurality of wells comprises a base, a conically-shaped wall and an outer opening, wherein the base has a substantially planar shape, and wherein further the diameter of the base is less than the diameter of the opening.

* * * * *